United States Patent
Eliasen

(10) Patent No.: US 9,744,343 B2
(45) Date of Patent: *Aug. 29, 2017

(54) VOLUME REDUCING RESERVOIR INSERT FOR AN INFUSION PORT

(75) Inventor: Kenneth Arden Eliasen, Wrentham, MA (US)

(73) Assignee: Primo Medical Group, Inc., Stoughton, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/477,997

(22) Filed: May 22, 2012

(65) Prior Publication Data

US 2012/0232501 A1    Sep. 13, 2012

Related U.S. Application Data

(63) Continuation of application No. 12/902,839, filed on Oct. 12, 2010, now Pat. No. 8,182,453, which is a continuation of application No. 10/931,890, filed on Sep. 1, 2004, now Pat. No. 7,811,266, which is a continuation-in-part of application No. 10/890,909, filed on Jul. 13, 2004, now abandoned.

(51) Int. Cl.
   *A61M 39/02*   (2006.01)

(52) U.S. Cl.
   CPC .............. *A61M 39/0208* (2013.01)

(58) Field of Classification Search
   CPC .......... A61M 39/0208; A61M 5/14276; A61M 2039/0238; A61M 2039/0211; A61M 39/04; A61M 2039/0223; A61M 2209/045; A61M 2039/0226; A61M 2039/0081; A61M 2039/0235; A61M 2205/582; A61M 2039/0258

USPC .... 604/288.01, 288.02, 288.04, 288.03, 175, 604/890.1, 891.1

See application file for complete search history.

(56) References Cited

U.S. PATENT DOCUMENTS

| | | | |
|---|---|---|---|
| 3,310,051 A * | 3/1967 | Schulte | 604/175 |
| 4,181,132 A | 1/1980 | Parks | |
| 4,190,040 A | 2/1980 | Schulte | |
| 4,382,445 A | 5/1983 | Sommers | |
| 4,445,896 A | 5/1984 | Gianturco | |
| 4,496,343 A * | 1/1985 | Prosl | A61M 5/14276 604/131 |
| 4,534,759 A * | 8/1985 | Trawoger | 604/117 |

(Continued)

FOREIGN PATENT DOCUMENTS

WO    9701370    1/1997

OTHER PUBLICATIONS

PCT International Search Report dated Nov. 21, 2001 issued in PCT Application No. PCT/US01/13749, 4 pages.

(Continued)

*Primary Examiner* — Imani Hayman
*Assistant Examiner* — Laura Schell
(74) *Attorney, Agent, or Firm* — Grossman Tucker Perreault & Pfleger PLLC

(57) ABSTRACT

An access portal is provided including a housing, a body defining a fluid reservoir, and a septum enclosing the fluid reservoir. A stem in fluid communication with the fluid reservoir extends from the fluid reservoir. The access portal also includes a reservoir insert disposed within the fluid reservoir, in which the reservoir insert decreases the fluid fill volume of the reservoir.

17 Claims, 12 Drawing Sheets

(56) References Cited

U.S. PATENT DOCUMENTS

| | | | |
|---|---|---|---|
| 4,543,088 A * | 9/1985 | Bootman et al. | 604/288.02 |
| 4,576,595 A | 3/1986 | Aas et al. | |
| 4,673,394 A | 6/1987 | Fenton, Jr. et al. | |
| 4,692,146 A | 9/1987 | Hilger | |
| 4,710,167 A | 12/1987 | Lazorthes | |
| 4,781,680 A | 11/1988 | Redmond et al. | |
| 4,802,885 A | 2/1989 | Weeks et al. | |
| 4,832,054 A * | 5/1989 | Bark | 128/899 |
| 4,840,615 A | 6/1989 | Hancock et al. | |
| 4,892,518 A | 1/1990 | Cupp et al. | |
| 4,904,241 A | 2/1990 | Bark | |
| 4,929,236 A | 5/1990 | Sampson | |
| 5,041,098 A | 8/1991 | Loiterman et al. | |
| 5,084,015 A | 1/1992 | Moriuchi | |
| 5,137,529 A * | 8/1992 | Watson et al. | 604/891.1 |
| 5,203,771 A | 4/1993 | Melker et al. | |
| 5,213,574 A | 5/1993 | Tucker | |
| 5,215,530 A | 6/1993 | Hogan | |
| 5,234,406 A | 8/1993 | Dransner et al. | |
| 5,281,199 A | 1/1994 | Ensminger et al. | |
| 5,295,658 A | 3/1994 | Atkinson et al. | |
| 5,306,255 A * | 4/1994 | Haindl | A61M 39/0208 |
| | | | 604/175 |
| 5,318,545 A | 6/1994 | Tucker | |
| 5,332,398 A | 7/1994 | Miller et al. | |
| 5,338,398 A | 8/1994 | Szwejkowski et al. | |
| 5,350,360 A | 9/1994 | Ensminger et al. | |
| 5,360,407 A | 11/1994 | Leonard | |
| 5,387,192 A | 2/1995 | Glantz et al. | |
| 5,391,801 A | 2/1995 | Sato et al. | |
| 5,399,168 A | 3/1995 | Wadsworth, Jr. et al. | |
| 5,417,656 A | 5/1995 | Ensminger et al. | |
| 5,476,460 A * | 12/1995 | Montalvo | 604/891.1 |
| 5,520,643 A | 5/1996 | Ensminger et al. | |
| 5,527,278 A | 6/1996 | Ensminger et al. | |
| 5,556,381 A | 9/1996 | Ensminger et al. | |
| 5,562,617 A | 10/1996 | Finch, Jr. et al. | |
| 5,562,618 A | 10/1996 | Cai et al. | |
| 5,613,945 A | 3/1997 | Cai et al. | |
| 5,647,855 A | 7/1997 | Trooskin | |
| 5,695,490 A * | 12/1997 | Flaherty et al. | 604/891.1 |
| 5,704,915 A | 1/1998 | Melsky et al. | |
| 5,718,682 A | 2/1998 | Tucker | |
| 5,718,692 A | 2/1998 | Schon et al. | |
| 5,792,104 A | 8/1998 | Speckman et al. | |
| 5,792,123 A | 8/1998 | Ensminger | |
| 5,797,879 A * | 8/1998 | DeCampli | 604/93.01 |
| 5,833,654 A | 11/1998 | Powers et al. | |
| 5,836,935 A * | 11/1998 | Ashton et al. | 604/891.1 |
| 5,843,069 A | 12/1998 | Butler et al. | |
| 5,848,989 A | 12/1998 | Villani | |
| 5,931,801 A | 8/1999 | Burbank et al. | |
| 5,951,512 A | 9/1999 | Dalton | |
| 5,954,691 A | 9/1999 | Prosl | |
| 5,989,206 A | 11/1999 | Prosl et al. | |
| 5,989,216 A | 11/1999 | Johnson et al. | |
| 6,007,516 A | 12/1999 | Burbank et al. | |
| 6,039,712 A | 3/2000 | Fogarty et al. | |
| 6,190,352 B1 * | 2/2001 | Haarala et al. | 604/93.01 |
| 6,213,973 B1 | 4/2001 | Eliasen et al. | |
| 6,471,689 B1 * | 10/2002 | Joseph | A61L 29/04 |
| | | | 424/424 |
| 6,478,783 B1 | 11/2002 | Moorehead | |
| 6,527,754 B1 | 3/2003 | Tallarida et al. | |
| 6,962,577 B2 | 11/2005 | Tallarida et al. | |
| 7,351,233 B2 | 4/2008 | Parks | |
| 2005/0014993 A1 * | 1/2005 | Mische | 600/40 |
| 2006/0224129 A1 | 10/2006 | Beasley et al. | |

OTHER PUBLICATIONS

PCT Written Opinion dated Dec. 19, 2002 issued in PCT Application PCT/US01/13749, 5 pages.
PCT Preliminary Examination Report dated May 28, 2003 issued in PCT Application PCT/US01/13749,2 pages.
European Examination Report dated Jul. 30, 2003 issued in European Patent Application No. 99 964 086.5, 11 pages.
U.S. Office Action dated Aug. 27, 2003 issued in U.S. Appl. No. 09/842,458, 8 pages.
U.S. Office Action dated Dec. 23, 2003 issued in U S. Appl. No. 09/842,458, 7 pages.
European Examination Report dated Mar. 9, 2004 issued in European Patent Application No. 99 964 086.5, 10 pages.
U.S. Notice of Allowance dated Oct. 15, 2004 issued in U.S. Appl. No. 09/842,458, 7 pages.
Australian Examination Report dated Jan. 21, 2005 issued in Australian Patent Application No. 2001257388, 2 pages.
U.S. Notice of Allowance dated Feb. 24, 2005 issued in U.S. Appl. No. 09/842,458, 6 pages.
European Examination Report dated Mar. 1, 2005 issued in European Patent Application No. 99 964 086.5, 10 pages.
European Examination Report dated Mar. 30, 2005 issued in European Patent Application No. 99 964 086.5, 10 pages.
European Decision to Refuse dated Dec. 15, 2005 issued in European Patent Application No. 99 964 086.5, 15 pages.
U.S. Office Action dated Feb. 28, 2007 issued in U.S. Appl. No. 10/374,000, 8 pages.
U.S. Office Action dated Aug. 28, 2007 issued in U.S. Appl. No. 10/374,000, 8 pages.
Canadian Office Action dated Oct. 16, 2007 issued in Canadian Patent Application No. 2,407,643, 2 pages.
U.S. Office Action dated Feb. 21, 2008 issued in U.S. Appl. No. 11/269,098, 19 pages.
U.S. Office Action dated Mar. 20, 2008 issued in U.S. Appl. No. 10/374,000, 7 pages.
U.S. Office Action dated Sep. 30, 2008 issued in U.S. Appl. No. 10/374,000, 8 pages.
U.S. Office Action dated Oct. 30, 2008 issued in U.S Appl. No. 11/269,098, 12 pages.
U.S. Office Action dated May 20, 2009 issued in U.S. Appl. No. 10/374,000, 10 pages.
U.S. Office Action dated Jun. 4, 2009 issued in U.S. Appl. No. 11/269,098, 11 pages.
Supplemental European Search Report dated Jun. 10, 2009 issued in European Patent Application No. 01 930 898.0, 4 pages.
European Examination Report dated Oct. 2, 2009 issued in European Patent Application No. 01 930 898.0, 4 pages.
U.S. Office Action dated Mar. 3, 2010 issued in U.S. Appl. No. 11/269,098, 15 pages.
U.S. Office Action dated Mar. 25, 2011 and issued in U.S. Appl. No. 12/778,093, 24 pages.
U.S. Office Action dated Oct. 17, 2011 issued in U.S. Appl. No. 12/778,093, 15 pages.
Access technologies, The V-A-Pu . . . Vascular Access and Beyond, downloaded from internet Jul. 28, 2009, http://www.norfolkaccess.com/VAPs.html, 4 pages.
SyncMedical, Innovative Surgical Devices, Primo Port Products, downloaded from internet Jul. 28, 2009, http://www.syncmedical.com/primo-port, 2 pages.
U.S. Office Action dated Apr. 20, 2016 issued in U.S. Appl. No. 13/855,058, 12 pages.
Office Action dated Jan. 24, 2017, issued in U.S. Appl. No. 13/855,058, 16 pages.

* cited by examiner

VOLUME REDUCING RESERVOIR INSERT FOR AN INFUSION PORT

CROSS-REFERENCE TO RELATED APPLICATIONS

This application is a continuation application under 37 CFR §1.53(b) of U.S. patent application Ser. No. 12/902,839 filed Oct. 12, 2010, now U.S. Pat. No. 8,182,453 which is a continuation of U.S. patent application Ser. No. 10/931,890 filed Sep. 1, 2004, now U.S. Pat. No. 7,811,266, which is a continuation-in-part of U.S. application Ser. No. 10/890,909, filed on Jul. 13, 2004, the entire disclosures of which are incorporated herein by reference.

FIELD

The present disclosure is generally directed at subcutaneously implantable vascular access portals. More specifically, the present disclosure is directed at vascular access portals having a reduced internal fluid fill volume.

BACKGROUND

Direct access to the vascular system is a quick and effective way to administer a variety of drug therapies, provide nutrition, and/or sample blood. Currently, regular access to the vascular system is gained by using a device specifically designed for this task. Several types or families of these devices exist in the market today. Among them are needles, catheters and a group of devices known as implanted access portals.

Vascular access has evolved through the years to improve treatment of a number of chronic and non-chronic diseases. Needles have been used for many years to inject vaccines and antibiotics or withdraw blood. Although still widely used today, needles have several limitations that do not allow them to be used with all therapies. In the early 1970's the use of vascular access catheters was perfected. Vascular access catheters allowed long term antibiotic, chemo, and nutritional therapies to be administered without having to change the access device. Additionally, vascular access catheters made it possible to introduce a medicament into a large enough vessel to allow the hemo-dilution required for some of the more toxic therapeutic drugs. This type of catheter provides a significant improvement over needles for long-term access, however, the external segment of such catheters may be prone to infection and requires constant maintenance. The latest development in vascular access is the implanted access portal, or ports. These portals eliminate the need for an external segment and therefore do not have the drawbacks of catheters.

Although considered new technology in the field of vascular access, implanted access portals have existed in the market for over 20 years. Use of these products has increased dramatically during this period because they are generally the device of choice for long-term vascular access. They are particularly suited for long-term use because the entire device is implanted under the skin. Implantability is one factor in the success of the implantable access portals because it allows the patient to perform ordinary daily tasks such as bathing and swimming without worrying about harming an external segment of an access device or increasing the chance of infection. Thus the quality of life for the patient is improved and the clinician is presented with fewer device related complications.

Typically implanted access portals consist of a housing, a self-sealing septum, and an attachable or pre-connected catheter. Portal housings can be made of a variety of materials including plastic, metal, or a combination of both. The self-sealing septum is generally made of an elastomer such as silicone. Catheters are also generally made of a highly flexible material such as silicone or polyurethane. Different materials are used to manufacture the components to achieve certain desired characteristics in the portal (i.e. plastic is not radiopaque, therefore the port will not show up on fluoroscopy).

Implanted access portals are also designed in such a way that their size (height and footprint), shape, and number of lumens are appropriate for the intended use. Number of lumens can be critical if a patient requires simultaneous infusion of incompatible solutions or isolation of blood sampling. As concurrent therapies become more popular the need for a wider variety of dual-lumen ports has increased.

During the life cycle of an implanted infusion portal a variety of complications can arise that may limit its functionality or render it useless altogether. Among these complications is "sludge buildup" or unwanted buildup of precipitate in the portal reservoir. This buildup is generally caused by improper or inadequate flushing of the portal. Typically portals are cleared or flushed immediately after aspiration or infusion. Routine flushing or maintenance is also performed when a portal is used infrequently or not at all. Flushing usually consists of injecting saline solution or saline solution containing an anti-coagulant, such as Heparin, through the reservoir and out the catheter into the vascular system. Generally the instructions for use will specify the volume of fluid and frequency required for proper maintenance.

BRIEF DESCRIPTION OF DRAWINGS

Features and advantages of the claimed subject matter are set forth by the description of exemplary embodiments consistent therewith, which description should be understood in conjunction with accompanying drawings, wherein:

DESCRIPTION

The present disclosure is directed at an implantable vascular access portal, herein also referred to as a port. Particularly, according to one aspect this disclosure is directed at an access port that may reduce the accumulation of precipitates, etc. within the port. According to another aspect, an access port may be provided having improved flushing efficiency. According to another aspect, the disclosed port may be designed to enhance flow of a fluid passing between the portal and an outlet.

Figure 1:
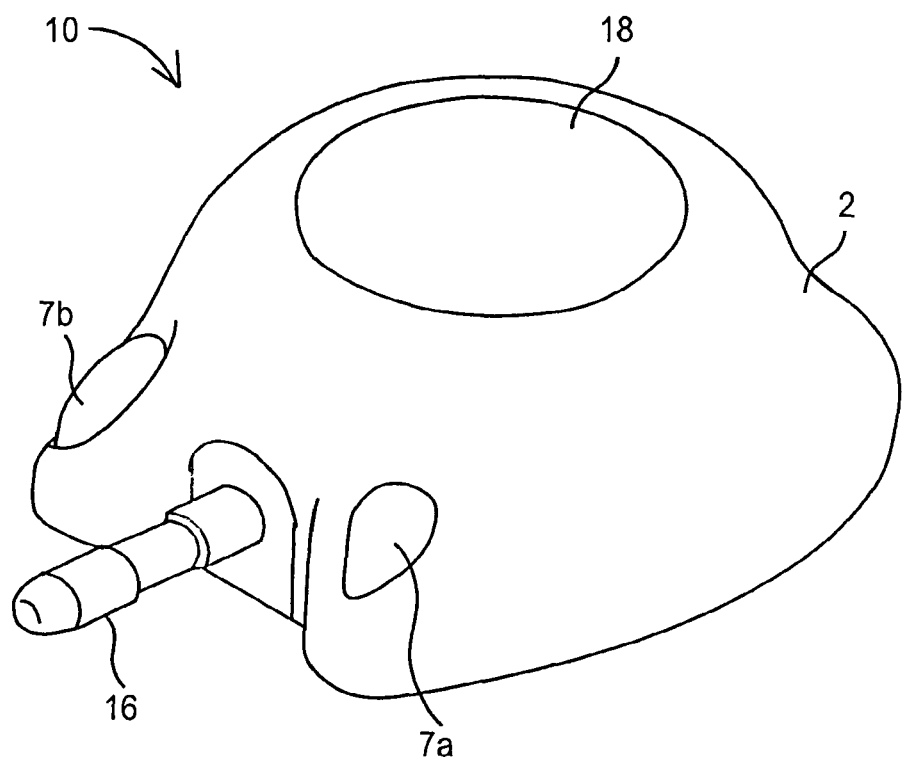
FIG. 1 is a perspective view of an exemplary embodiment of a vascular portal according to the present disclosure.
Figure 2:
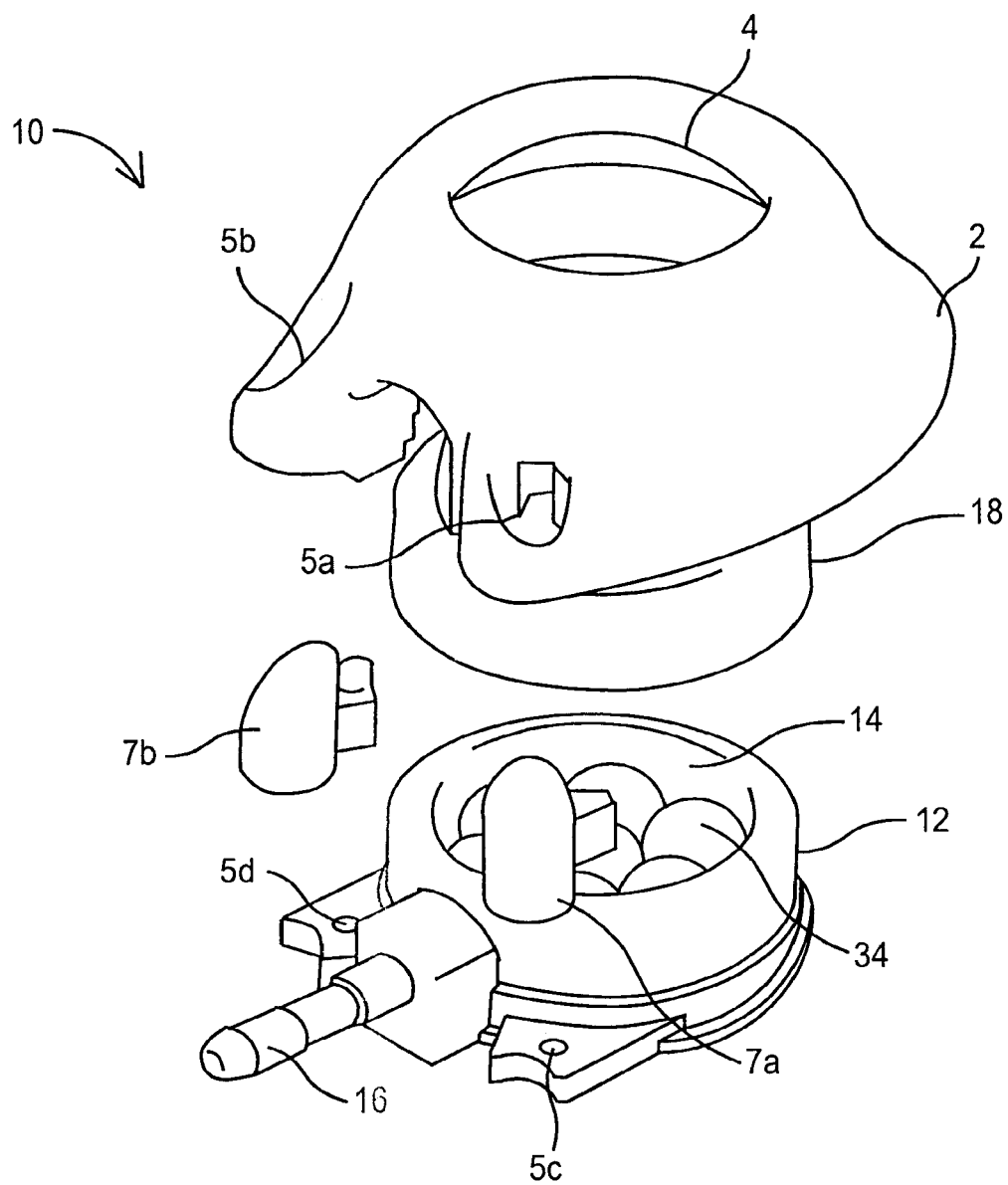
FIG. 2 is an exploded perspective view of the exemplary vascular portal of FIG. 1
Figure 3:
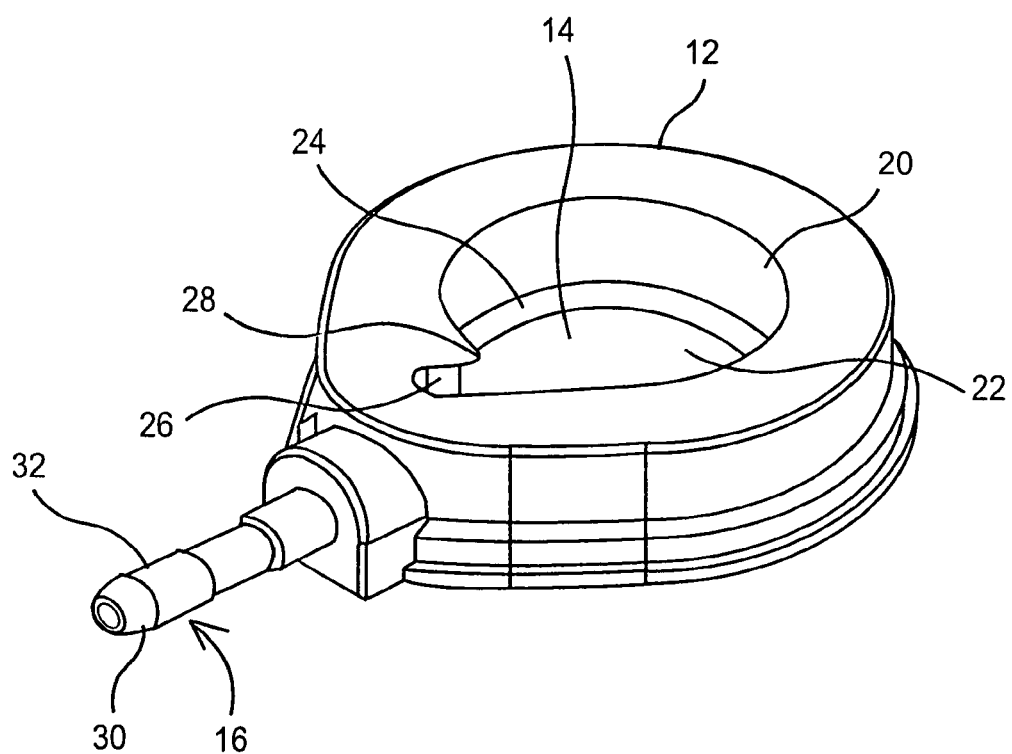
FIG. 3 is a perspective view of a body portion of one exemplary embodiment of a vascular access portal according to the present disclosure.

Turning to FIGS. 1 and 2, an exemplary access portal 10 consistent with the present disclosure is illustrated. As shown, the access portal 10 may generally include a housing 2, a body portion 12, a stem 16 and a septum 18. The housing 2 may define an opening 4 on a top surface thereof. The opening 4 in the housing 2 may permit access to a reservoir 14 defined in the body portion 12. The reservoir may be enclosed by the septum 18. The septum 18 may be disposed over the reservoir 14 between the body portion 12, and the housing 2.

The housing 2 may be constructed of any suitable biocompatible material, including polymeric materials, metallic materials, and ceramics. For example, the housing may conveniently be injection molded from a polymeric material and may generally define the overall profile and geometry of the access portal 10. The housing 2 may include a rounded or angled margin around the opening 4 to urge a needle downward toward the septum 18 and reservoir 14 covered thereby. This feature may reduce errant entry of needles within the septum 18.

The housing 2 may be assembled to the body 12 using a variety of techniques. As illustrated in FIG. 2, the housing 2 and the body 12 may include cooperating snap-fit features (not shown) or press-fit features. Accordingly, the housing 2 and body 12 may snap or press together. In addition, or as an alternative, to press or snap-fit assembly, the housing 2 and body 12 may be adhesively bonded together or welded, etc.

As shown, the access portal 10 may also include suture holes 5a-b extending through the housing 2 and corresponding suture holes 5c-d extending through the body 12. The suture holes 5a-d may allow the access portal 10 to be secured in a desired location within a patient. The access portal 10 may be secured by suturing through the suture holes 5a-d and tissue at the desired implantation site of the portal 10. Suture plugs 7a-b may be received in at least the suture holes 5a-b in the housing 2. The suture plugs may be employed to prevent the ingrowth and/or accumulation of tissue or other biometric material in the suture holes 5a-b of the housing 2. The suture plugs 7a-b may also be configured to be at least partially received in the suture holes 5c-d of the body 12. The suture plugs 7a-b may be formed of an elastomeric material, e.g., silicone, such that the suture plugs 7a-b may be penetrated with a suture needle and receive a suture passing through the plugs 7a-b. The elastomeric material may conform around the a suture passing therethrough The body 12 may be formed from any suitable biocompatible material. Exemplary materials may include polymeric materials, stainless steel, titanium, ceramic, etc. The body 12 may also be formed from more than one material. For example, the body 12 may include a biocompatible polymer having a stainless steel, titanium, or ceramic insert defining at least a portion of the reservoir 14.

The stem 16 may provide an outlet from the reservoir 14, allowing fluids to be delivered to a predetermined location in the body. In a similar manner, the stem 16 may allow fluids to be delivered from a predetermined location in the body to the reservoir 14, e.g., to permit aspiration. Generally, delivery of fluids between the access port 10 and a predetermined location in the body may be accomplished, for example, by transporting the fluid through a catheter (not shown). It should be understood that a catheter may be implanted in the body of a patient extending between the portal site and the predetermined location in the body of the patient. Accordingly, the stem 16 may be configured to be received in a lumen of a catheter. The distal end of the stem 16 may include a tapered lead in 30. The distal end of the stem 16 may also include a bullet 32 or a barb for retaining a catheter to the stem 16.

The septum 18 generally encloses the reservoir 14, thereby retaining contents of the reservoir 14. Additionally, the septum 18 may permit the reservoir 14 to be accessed, e.g., transcutaneously using a hypodermic needle. Access to the reservoir 14 may permit the delivery of fluids to, or extraction of fluids from, the portal 10. Consistent with the function of providing access to the portal 10, the septum 18 may be formed from a needle penetrable material that is self sealing. Exemplary septum materials may include biocompatible elastomers, such as silicone, polyurethane, etc.

Consistent with one embodiment, the septum 18 may be compressed against the body 12 by the housing 2 sufficiently to seal the septum 18 to the body 12 around the perimeter of the reservoir 14. Accordingly, the need for adhesives or sealants between the septum 18 and body portion 12 may be avoided. However, adhesives or sealants may be used between the septum 18 and the body portion 12 consistent with the present disclosure.

Figure 4:
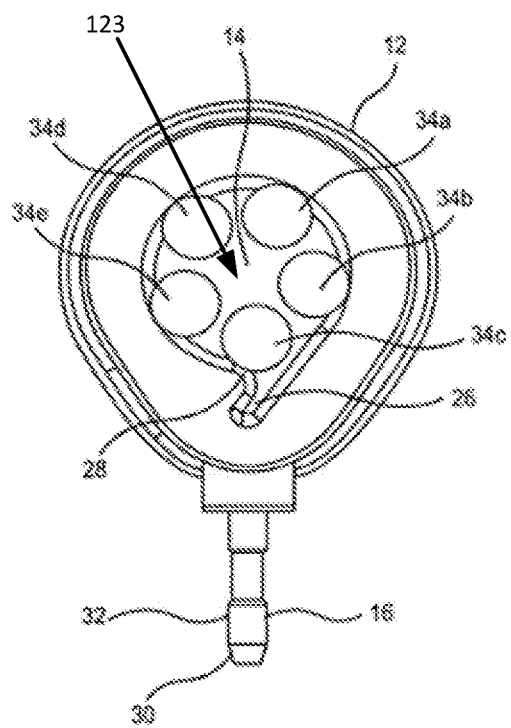
FIG. 4 is a plan view of a body portion of an exemplary access port shown in FIG. 3.

In plan view, the reservoir 14 of the exemplary access portal 10 may be provided having a generally circular shape, as shown in FIG. 4. The illustrated circular shape is merely exemplary, however. The reservoir 14 may be provided having various other shapes, such as an oval. The reservoir 14 may generally be defined by a sidewall 20 and a bottom 22. As shown the side wall 20 and the bottom 22 may meet in a radiused junction 24. The radiused junction 24 may reduce hang-up or stagnation of fluid passing into or out of the reservoir 14.

The reservoir 14 may include an outlet passage 26 extending from the reservoir 14 and in communication with the stem 16. The outlet passage 26 may extend from the reservoir 14 at an angle relative to the sidewall 20. As best seen in FIG. 4, in the illustrated exemplary embodiment the outlet passage 26 may extend from the reservoir 14 to provide a generally tangential outlet passage. The angled outlet passage 26 may facilitate ingress and egress of fluids into and out of the reservoir 14 through the passage 26 by providing a smooth passage and minimizing hang-up that may be associated with hard corners. Also as shown, a rounded transition 28 may be provided between the passage 26 and the reservoir 14. The rounded transition 28 between the reservoir 14 and the passage 26 may facilitate smooth flow between the reservoir 14 and passage 26 without the occurrence of hang-up along the flow path. The combination of the angled passage 26 and the rounded transition 28 may, therefore, reduce the occurrence of hang-up and/or dead spots, i.e., regions that are not readily cleared by the flow of fluid through the access portal, adjacent the passage 26. While the passage 26 of the illustrated embodiment is shown as a generally linear extension, it should be understood that the passage 26 may be an arcuate extension.

The radiused junction 24 between the sidewall 20 and bottom 22 of the reservoir may provide a smooth transition for fluid moving in the reservoir 14. The radiused junction 24 may also reduce hang-up of fluid, i.e., localized stagnation of fluid. The combination of the angled orientation of the outlet passage 26 and the rounded junction 28 between the passage 26 and the reservoir 14, as well as the radiused junction 24 between the sidewall 20 and bottom 22 of the reservoir 14, may all work together to reduce hang-ups and/or regions of stagnation within the access portal 10 may produce a number of effects.

Various fluids that may be infused or aspirated using an access portal may produce a precipitate or a residue if they are allowed to stagnate. As one example, any blood that becomes hung-up in the access portal 10, or is otherwise allowed to stagnate may coagulate inside the reservoir 14. The radiused junction 24 between the bottom 22 and sidewall 20 of the reservoir 14, as well as the angled arrangement of the outlet passage 26 and the rounded transition 28 into the passage 26 may generally reduce turbulent flow of fluids entering or exiting the reservoir. Additionally, at least some of these aspects of the exemplary port may also reduce the hang-up of fluids or stagnant regions within the reservoir 14. Reducing turbulence in fluids entering and/or exiting the reservoir 14 and reducing hang-up or stagnant regions may facilitate efficient clearing of fluids from the reservoir 14 and flushing of the reservoir 14. Accordingly, the accumulation of precipitates in the access portal 10 may also be reduced.

Flushing an access portal 10 may include introducing a flushing fluid into the reservoir 14 of the access portal 10. The flushing fluid introduced into the reservoir 14 may displace any fluid, and/or any solid matter, e.g., precipitate, initially in the reservoir out of the access portal 10. The displaced fluid may pass from the access portal 10 into the vascular system of the patient. During flushing, the flushing fluid may also mix with the fluid initially in the reservoir 14. Because of the mixing between the flushing fluid and the fluid initially in the reservoir 14, it may be necessary to flush the portal 10 with a quantity of flushing fluid equal up to several times the volume of the portal 10.

According to another aspect, the disclosure is directed at an access port 10 that provides improved flushing efficiency by reducing the fluid fill volume, e.g., free volume. As used in any embodiment herein, the fluid fill volume of the access portal is the volume of fluid that may be contained in the portal. Consistent with the exemplary embodiment, the fluid fill volume of the reservoir 14 may be reduced without reducing the depth of needle penetration or the area of the reservoir 14 that may receive a needle.

Turning to FIG. 4, the illustrated exemplary portal 10 includes five spherical volume reduction members 34a-34e disposed in the reservoir 14. The volume reduction members 34a-34e may act to reduce the fluid fill volume of the reservoir 14. The volume reduction members 34a-34e may be retained in the reservoir 14 by the septum (not shown in FIG. 4). Additionally, as shown the volume reduction members 34a-34e may be sized and/or shaped to prevent the volume reduction members 34a-34e from obstructing the outlet passage 26. The volume reduction members 34a-34e may be formed from any suitable material, including glass, plastic, stainless steel, titanium, ceramic, etc. According to one embodiment, the volume reduction members 34a-34e may be formed from a hard material that is not prone to producing debris when subjected to needle strikes.

In the illustrated embodiment the volume reduction members 34a-34e are disclosed having a spherical shape. It should be understood, however, that the spherical shape is not essential. The volume reduction members 34a-e may be provided in various other shapes. For example, the volume reduction members 34a-e may be prismatic bodies, cylinders, egg shaped, etc. Similarly, while the exemplary access portal 10 includes five volume reduction members 34a-34e any number of members may be used to provide a reduction in the fluid fill volume of the access portal. The volume reduction members 34a-e may generally define a central region 123. The central region 123 may extend unobstructed from the base of the fluid reservoir 14 to the septum 18.

Consistent with one embodiment, in addition to reducing the fluid fill volume of the reservoir 14, it may also be desirable to minimize the surface area of contact by a fluid in the reservoir 14. As used herein, the surface area of contact by a fluid is the total surface area of the portal 10 and components thereof contacted by a fluid within the reservoir 14. The surface area of contact by a fluid may include the surface area of the reservoir and the surface area of any volume reduction members disposed within the reservoir 14. According to one aspect, reducing the surface area of contact by a fluid may facilitate flushing by reducing the surface area within the reservoir to which a fluid may adhere, build-up on, or otherwise resist removal from. For example, blood within the reservoir 14 of the access portal 10 may stick to or coat the interior surface of the reservoir 14 and the outer surface of any volume reducing members 34a-34e disposed within the reservoir 14. Accordingly, the volume of fluid required to adequately flush the portal 10 may increase with an increase in the surface area of contact by a fluid in order to remove the fluid from any surfaces within the reservoir contacted by the fluid.

Consistent with the foregoing aspect, an embodiment of an access portal 10 herein may be provided in which the collective surface area of the volume reduction members 34a-34e may be relatively small. As also discussed above, however, an embodiment of an access portal 10 herein may be provided in which the volume of the reservoir 14 is reduced. Accordingly, the collective volume to surface area ratio of all of the volume reduction members 34a-34e together may be relatively large. The collective volume to surface area ratio of spherical volume reduction members 34a-34e of the illustrated embodiment may be increased by increasing the size of each of the volume reduction members 34a-34e. In the case of the illustrated access portal 10 the minimum dimension of the reservoir 14 may be the height of the reservoir 14 between the bottom 22 of the reservoir and the underside of the septum 18. Therefore, the size of the volume reduction members 34a-34e may be increased by providing the volume reduction members 34a-34e having a diameter that is equal to, or just slightly less than, the height of the reservoir 14 between the bottom 22 and the underside of the septum 18. For example, the volume reduction members may have at least one dimension approximately equal to a distance between the base region of the fluid reservoir and the underside of the septum. In addition to providing the largest individual volume reduction members 34a-34e, may increase the volume to surface area ratio and may also provide the fewest volume reduction members 34a-34e.

According to one embodiment the volume reduction members 34a-34e may be movable within the reservoir 14. Consistent with this embodiment, the volume reduction members 34a-34e may be displaced under an applied load. For example, when the portal 10 is accessed by a needle inserted through the septum 18, the needle may strike one of the volume reduction members 34a-34e. If the volume reduction members 34a-34e are movable within the reservoir the volume reduction members 34a-34e may be displaced by the force of the needle. Accordingly, the depth of penetration of a needle accessing the portal is not restricted in the exemplary embodiment.

Allowing the volume reduction members 34a-34e to be moveable within the reservoir 14, so that volume reduction members 34a-34e may permit the access portal 10 to be access by a needle inserted through the septum 18, may not only require that the volume reduction members 34a-34e are not fixed to the reservoir 14 or to the septum 18, but may also require at least some spacing in between the volume reduction members 34a-34e. For example, referring to the embodiment shown in FIG. 4, volume reduction members 34a-34e may be positioned generally around the circumference of the reservoir 14, and the volume reduction members 34a-34e are at least slightly spaced apart. Accordingly, the volume reduction members 34a-34e may be displaced by the force of a needle inserted into the reservoir 14. In the illustrated embodiment, however, a volume reduction member is not disposed in the central portion of the reservoir 14. The circumferentially disposed volume reduction members 34a-34e may prevent a volume reduction member disposed in the central portion of the reservoir from moving under contact from a needle accessing portal 10. According to other embodiments, however, the number and/or size of the volume reduction members 34a-34e and/or the diameter of the reservoir 14 relative to the diameters of the volume reduction members 34a-34e may permit a centrally disposed volume reduction member to be employed.

Consistent with the foregoing, an embodiment of the present disclosure may provide volume reducing members having a relatively large cumulative volume and a relatively small cumulative surface area. Additionally, the volume reducing members may be provided having sufficient freedom of movement to allow the volume reducing members to move out of the way of a needle entering the reservoir. Consistent with such an embodiment, the volume reducing members may provide a reduction in the volume of the reservoir generally equal to, or less than, 40%. In further embodiments, the volume reducing members may provide a reservoir volume reduction in the range of between about 40% to about 20%.

According to another embodiment, the volume reduction members 34a-34e may be non-movable within the reservoir 14. According to such an embodiment, if a needle being inserted to access the portal 10 strikes one of the volume reduction members 34a-34e the needle may deflect around the object. For example, in the case of the exemplary spherical volume reduction members 34a-34e, a needle striking one of the volume reduction members 34a-34e the tip of the needle may slide along the arcuate surface of the volume reduction members 34a-34e, causing the needle to deflect around the volume reduction member 34a-e. Deflecting around a volume reduction member 34a-34e within the reservoir 14 may involve changing the angle of attack of the needle, whereby the needle may extend into the reservoir into a space between the volume reduction members 34a-34e. Needle insertion may be facilitated by providing the non-movable volume reduction members 34a-e having an angled or arcuate upper surface. For example, the volume reduction members 34a-e may be provided as pyramids, cones, spheres, hemi-spheres, etc.

In a portal 10 having non-movable volume reduction members 34a-e, the volume reduction members 34a-e may be integrally formed with the body portion 12. For example, the volume reduction members 34a-e may be formed as projections from the bottom 22 of the reservoir 14, from the sidewall 20 of the reservoir 14, or a combination of both. According to another embodiment, the non-movable volume reduction members 34a-e may be separate components that are positioned in a non-movable condition within the reservoir.

Reducing the fluid fill volume of the reservoir consistent with this preceding disclosure may allow the portal reservoir to be cleared or flushed with less fluid. For example, a reservoir having a total volume of 1 ml achieves a ten times exchange from a flushing volume of 10 ml of saline. If the fluid fill volume of the reservoir is reduced to 0.5 ml, flushing the port with 10 ml of saline will achieve a twenty times exchange. Accordingly, by reducing the fluid fill volume of the reservoir, the port may be more thoroughly flushed without introducing a greater amount of fluid into the patient. Additionally, if the access portal is used for aspiration, a smaller fluid fill volume of the reservoir may allow less fluid to be drawn into the reservoir.

Figure 5:
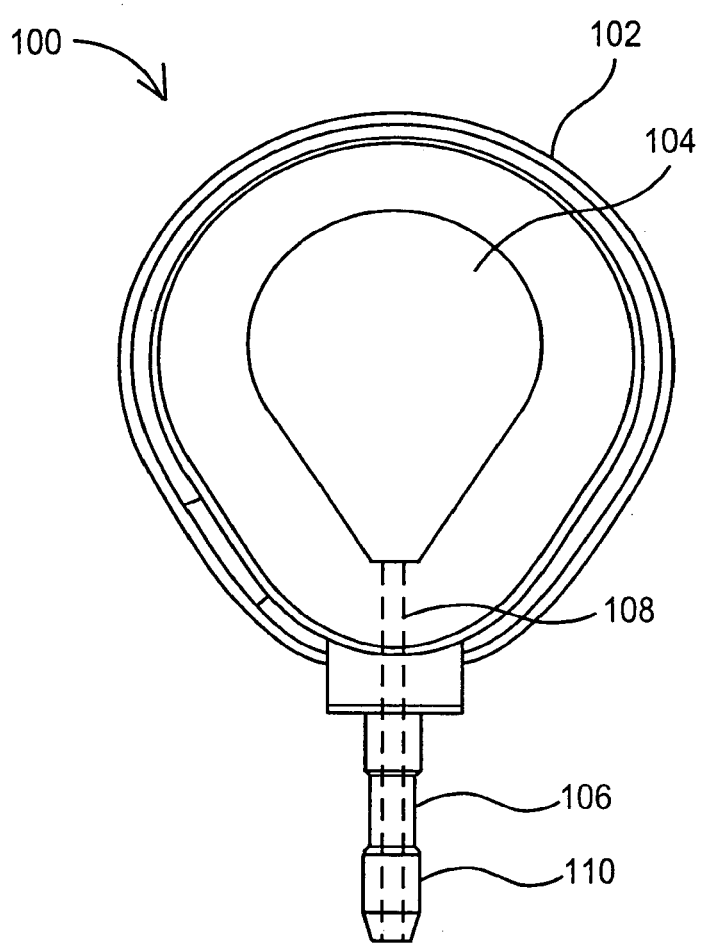
FIG. 5 shows another embodiment of an access port in plan view.
Figure 6:
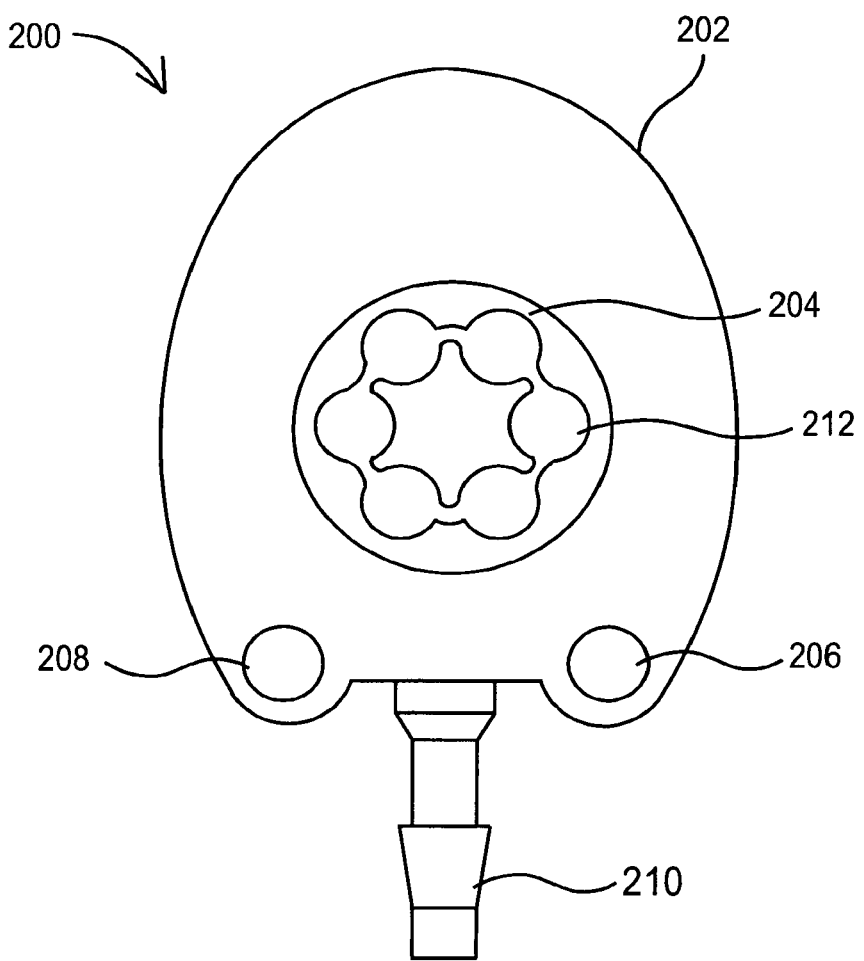
FIG. 6 shows another embodiment of an access port in plan view.

Turning next to FIG. 5, another embodiment of an access portal 100 providing efficient flushing is shown. The illustrated access portal 100 may generally include a body 102 defining a fluid reservoir 104 therein. The access portal 100 may also include a stem 106 in fluid communication with the fluid reservoir 104. As with the preceding embodiments, the access portal consistent with the embodiment illustrated in FIG. 5 may additionally include a housing member.

As with previously described embodiments, the various components of the access portal 100 may be produced from a variety of biocompatible materials including metallic materials, ceramic materials, polymeric materials, and combinations thereof. For example, the body 102 of the access portal 100 may be formed from a polymeric material and may include a metallic cup, liner, or bottom plate making up at least a portion of the reservoir 104, thereby reducing the production of debris resulting from needle strikes in the reservoir 104. Consistent with other embodiments, the entire body 102 of the access portal 100 may be formed from a polymeric material, either as a unitary construction or as an assembly of components. Various other materials and constructions may also suitably be employed for producing an access portal 100 consistent with the present disclosure.

As with previous embodiments, the fluid reservoir 104 of the access portal 100 may be configured having an open top to provide access to the reservoir 104. While not shown in the plan view illustration, the access portal 100 may additionally include a septum disposed over the fluid reservoir 104. The septum may restrict fluid passage to and from the reservoir 104 through the open top thereof, but may allow the reservoir 104 to be accessed, e.g., by a needle penetrating the septum.

The stem 106 may provide fluid communication between the fluid reservoir 104 and the exterior of the access portal 100, thereby allowing fluids to be delivered from the fluid reservoir 104 to a predetermined location in the body, or to be extracted from a predetermined location in the body through the fluid reservoir 104. A fluid passageway 108 may be provided extending from the fluid reservoir 104 and through the stem 106, thereby providing fluid communication from the fluid reservoir 104. As with previous embodiments, the stem 106 may be provided with a barbed or a bulbous end portion 110 to facilitate securing a catheter (not shown) to the stem 106. A catheter secured to the stem 106 may be implanted in the body of a patient extending from the access portal 100 to a predetermined location in the body of the patient. Accordingly, the catheter may allow fluid to be delivered to, or extracted from, such predetermined location in the body of a patient.

Consistent with the illustrated embodiment, the fluid reservoir 104 may be provided having a teardrop shape in plan view. That is, with reference to FIG. 5, the fluid reservoir 104 may be shaped having a generally arcuate contour that converges towards a single point on one side. Consistent with the illustrated embodiment, the fluid reservoir 104 may have an arcuate shape that converges toward a single point in the region of the fluid passageway 108 of the stem 106. Accordingly, fluid introduced into the fluid reservoir 104, e.g. through the septum by a needle, may be directed toward the fluid passageway 108 by the contour of the fluid reservoir 104. The continuous contour of the fluid reservoir 104 may have few, or no, hard angles or inside corners. The lack of hard angles may promote smooth transfer of fluid into and out of the reservoir 104, and may minimize the occurrence of hang-up. For example, fluid may pass between the fluid reservoir 104 and the fluid passageway 108 without becoming entrapped in regions that prevent clearing of the reservoir 104 and/or aspiration of fluids through the reservoir 104.

Consistent with a further aspect, the junction between the bottom of the fluid reservoir 104 and the sidewalls of the reservoir 104 may be rounded, thereby reducing any flow drag, or hang-ups. Similarly, the side of the septum facing the interior of the fluid reservoir 104 may include a contoured or rounded transition between the septum and the sidewalls of the fluid reservoir 104. The contour or rounded transition may also eliminate a hard corner between the septum and the sidewall of the reservoir 104. According to one embodiment, the fluid reservoir 104 may be tapered across the depth thereof and/or include a tapered region adjacent the fluid passageway 108 in communication with the reservoir 104. The tapering of the fluid reservoir 104 may generally provide a smooth transition between the reservoir 104 and the fluid passageway 108. Accordingly, the geometry of the fluid reservoir 104 and the transition between the fluid reservoir 104 and the fluid passageway 108 may be configured to minimize or eliminate any features that may cause hang-up and/or may be optimized to reduce or eliminate any causes of turbulent flow between the fluid reservoir 104 and the fluid passageway 108.

In addition to including a reservoir 104 having a geometry that may reduce or eliminate hang-up and turbulent flow, the access portal 100 may also include one or more volume reducing members disposed within the reservoir 104. Accordingly, in addition to eliminating impediments to smooth flow into and out of the reservoir 104, the access portal may also provide a reduced internal volume. The one or more volume reducing members may be configured and arranged in a manner as described with reference to the preceding embodiments.

Turning to FIGS. 6 through 9, another embodiment of an access portal 200 is shown. As with previous embodiments, the access portal 200 may generally include a housing 202 that may include an opening providing access to a fluid reservoir 204. The housing 202 may additionally have one or more suture holes 206, 208. The fluid reservoir 204 may include a volume reducing reservoir insert 212. The access portal 200 may additionally include a stem 210 in fluid communication with the reservoir 204.

Figure 7:
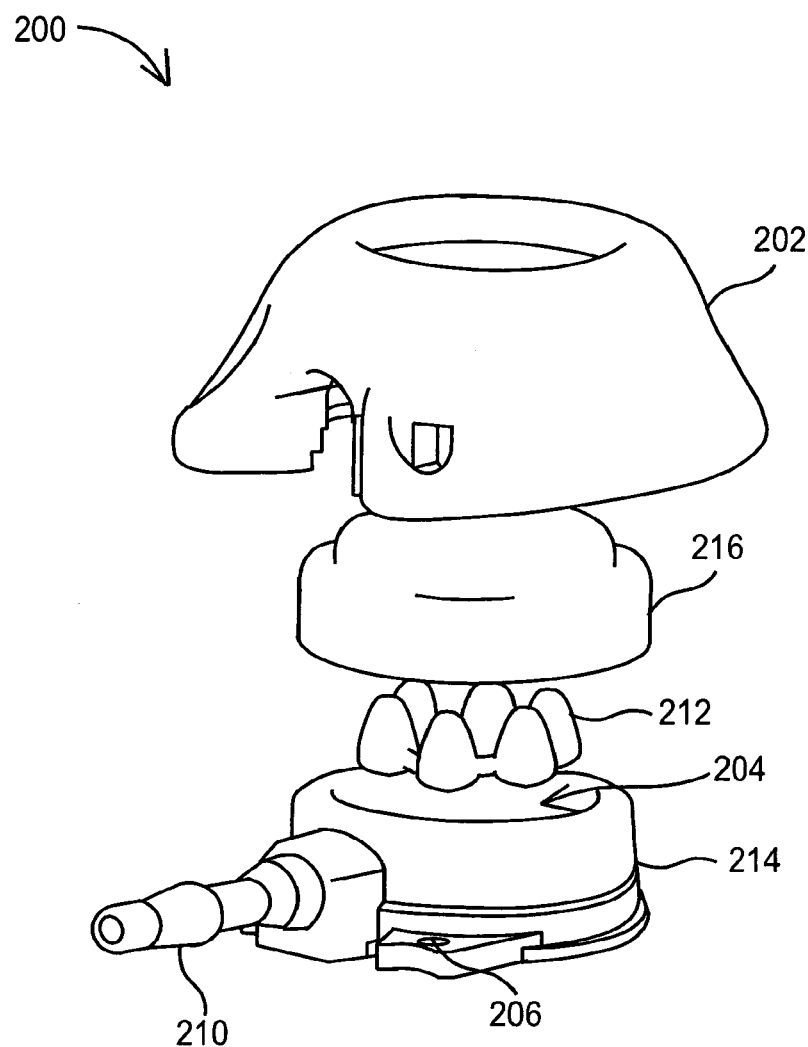
FIG. 7 is an exploded perspective view of the access port illustrated in FIG. 6.
Figure 8:
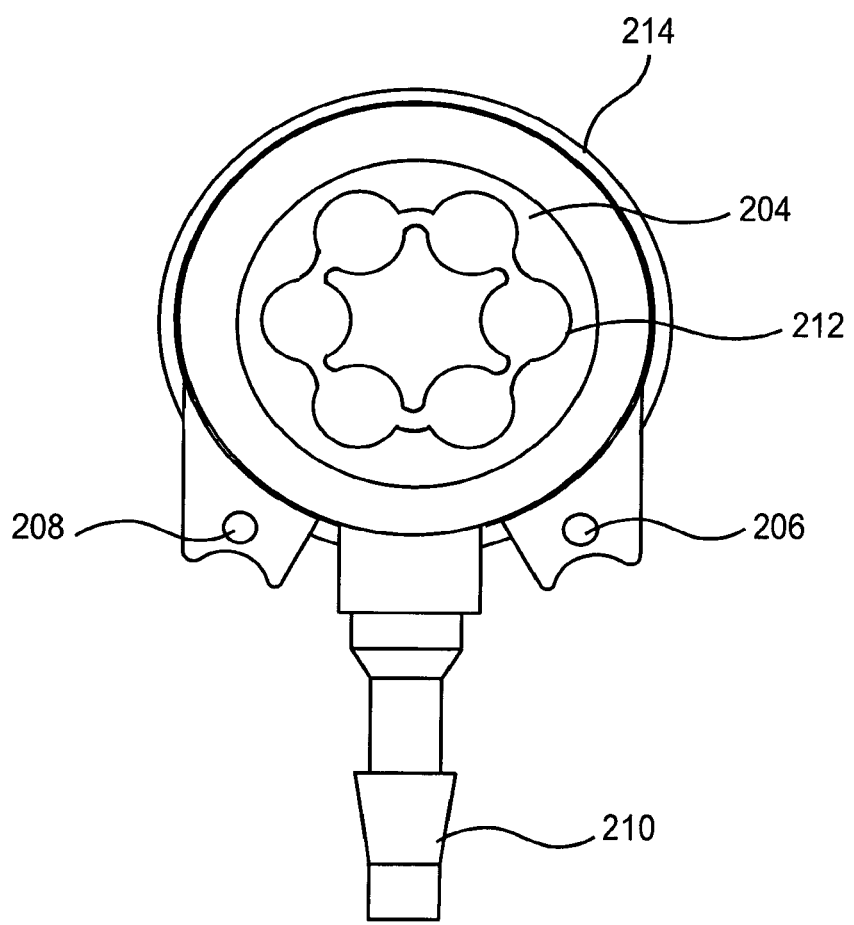
FIG. 8 is a plan view of the access port of FIG. 6 not including a housing component.
Figure 9:
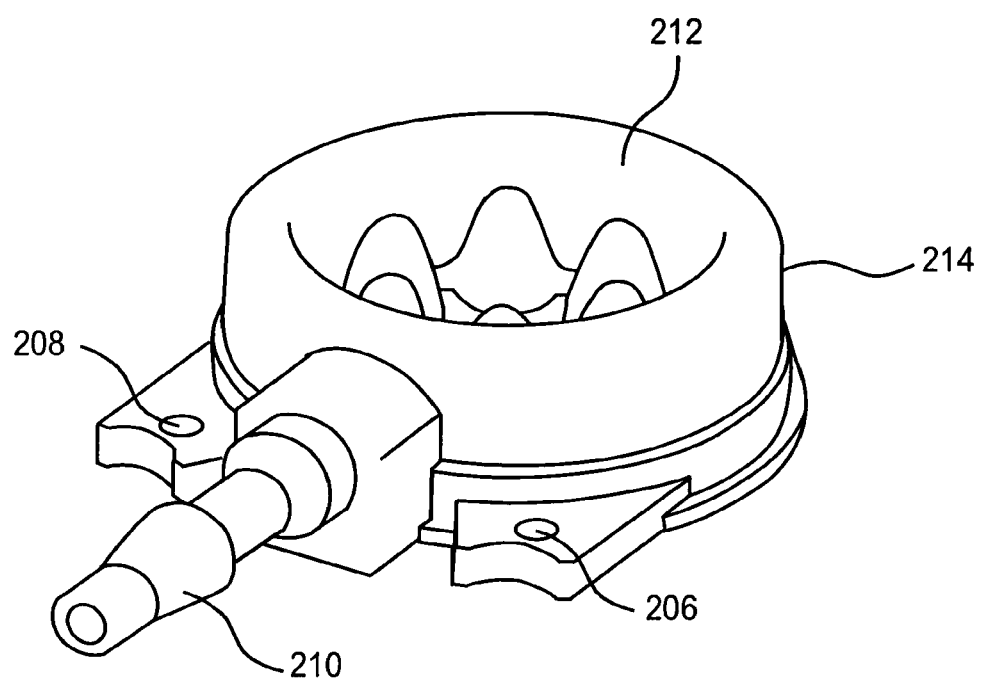
FIG. 9 is a perspective view of the access port depicted in FIG. 8.

Referring to the exploded view of the access portal 200 in FIG. 7, the housing 202 may be configured to at least partially surround a body member 214. The body member 214 may define the reservoir 204 which is accessible through the opening in the housing 202. A septum 216 may be disposed between the housing 202 and the body 214. When the access portal 200 is in an assembled condition the septum 216 may be disposed over and may seal a top portion of the reservoir 204.

Consistent with the previously described embodiments, the housing 202 may generally be configured to provide the access portal 200 with a contoured outer profile. The contoured profile provided by the housing 202 may improve the comfort of the access portal 200 when it is implanted into a patient. Additionally, the contoured profile may also aid in positioning the access portal 200 in a desired location within a patient through a minimally sized incision. The housing 202 may be manufactured from any suitable biocompatible material, including polymeric materials, metallic materials, ceramic materials, combinations thereof, etc.

The septum 216 may permit the reservoir to be accessed by a needle. Accordingly, the septum 216 may be a needle penetrable biocompatible material. The septum 216 may also be adapted to seal the upper opening of the reservoir 204. According to specific embodiments, the septum 216 may be a self sealing elastomeric and/or low durometer material such as silicone.

As with previous embodiments, the stem 210 may include a lumen in fluid communication with the reservoir 204. Additionally, the stem 210 may include a barb, or similar feature, adjacent the distal end of the stem 210. The barb may allow a catheter to be secured to the stem 210 for communicating fluid between the reservoir 204 and a predetermined location in the body of a patient.

Consistent with the illustrated embodiment, the access portal 200 may include a volume reducing reservoir insert 212. The reservoir insert 212 may reduce the fluid fill volume of the reservoir 204, similar to the previously discussed volume reducing members. Consistent with this aspect of the disclosure, reservoir insert 212 may be configured to reduce the fluid fill volume of the reservoir 204 between about 5% to about 95%, as well as any values therebetween. According to one embodiment, the reservoir insert 212 may reduce the fluid fill volume of the reservoir 204 by between about 20% to about 80%. According to a further embodiment, the reservoir insert 212 may reduce the fluid fill volume of the reservoir 204 by between about 20% to about 40%. As mentioned previously, the reservoir insert 212 may be configured to reduce the fluid fill volume of the reservoir 204 by any desired amount within the disclosed ranges.

Figure 10:
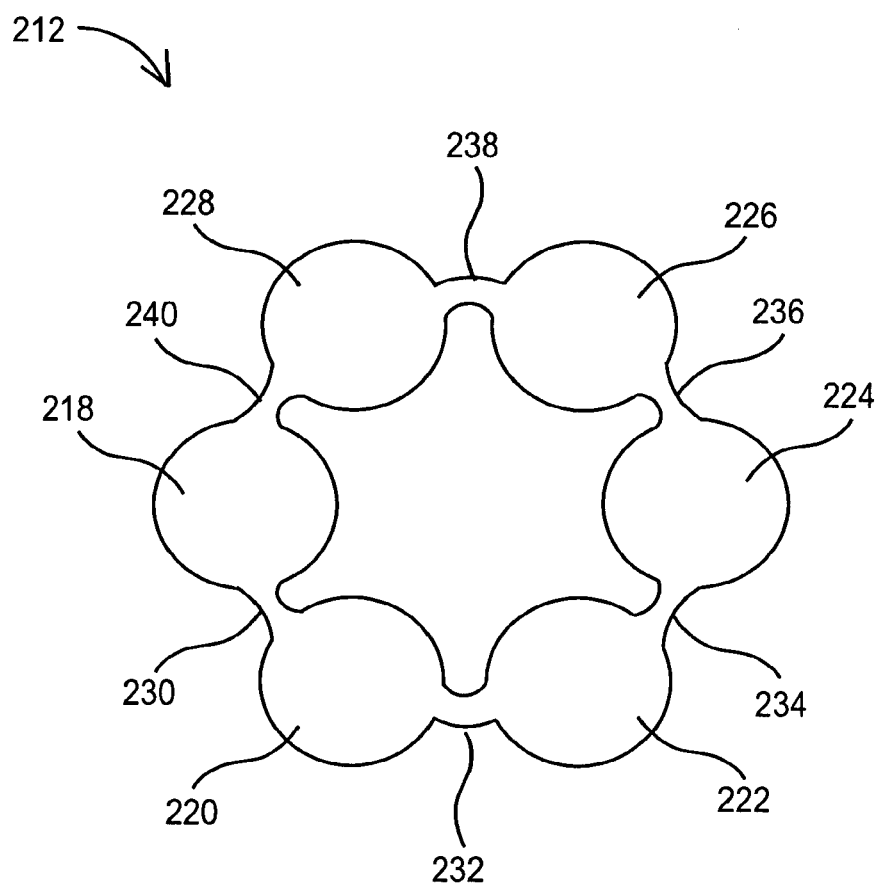
FIG. 10 is a top view of an embodiment of a volume reducing reservoir insert.
Figure 11:
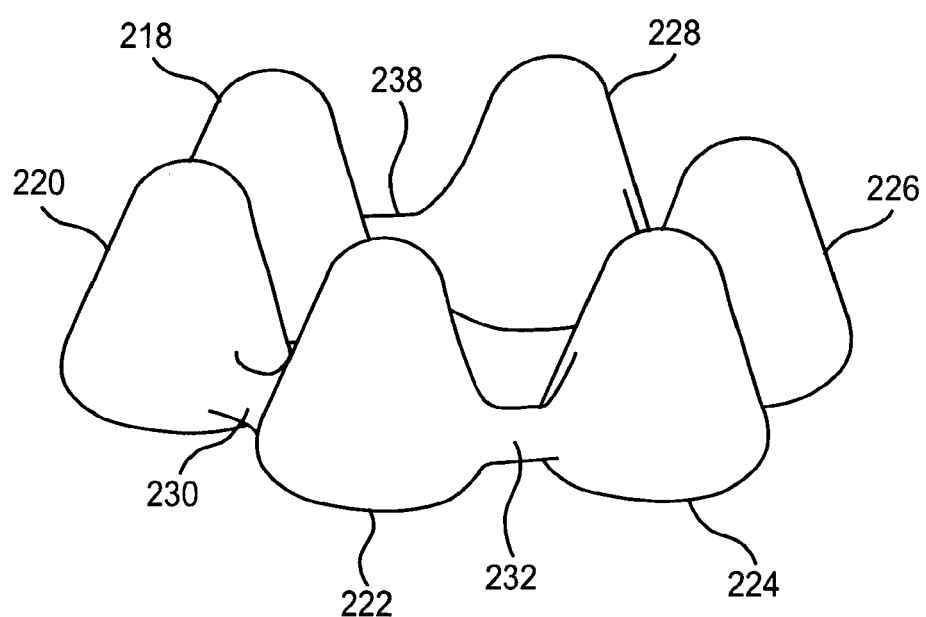
FIG. 11 is a perspective view of the volume reducing reservoir insert of FIG. 10.

With reference to FIGS. 10 and 11, the illustrated reservoir insert 212 may include a ring member having a plurality of protuberances 218-228 linked by webs 230-240. In the illustrated embodiment at least a portion of the protuberances 218-228 have a generally conical shape. The top portion of the generally conical protuberances 218-228 may be radiused, as shown, flat, or pointed. Additionally, the bottoms of the protuberances 218-228 may be arcuate, for example, hemi-spherical. Alternatively, the bottom could be flat. Such an arcuate bottom, while not necessary, may reduce the occurrence of material, such as precipitate, becoming trapped between the protuberances 218-228 and the floor of the reservoir 204. This aspect is not, however, critical within the context of the present disclosure.

The conical shape of the protuberances 218-228 may allow a needle entering the reservoir 204 through the septum 216 to slide along or around the protuberances 218-228 without become blocked or damaged. Entrance of a needle into the reservoir 204 may also be facilitated by providing the reservoir insert 212 in a movable condition within the reservoir 204. Movement of the reservoir insert 212 may be achieved through translation and/or through rotation. If the reservoir insert 212 is contacted by a needle entering the reservoir 204 the reservoir insert 212 may move to one side of the reservoir 204, thereby allowing entrance of the needle. Additionally, or alternatively, if the reservoir insert 212 is contacted by a needle entering the reservoir 204 the reservoir insert 212 may rotate out of the path of the needle to allow the needle to access the reservoir 204. Rotation of the reservoir insert 212 may be achieved even if the reservoir insert 212 is not sized to permit translation of the reservoir insert 212 within the reservoir.

Movement of the reservoir insert 212 may also be facilitated by minimizing friction between the reservoir insert 212 and the reservoir 204. As a further aspect of providing the protuberances 218-228 having an arcuate bottom, the contact area between the protuberances 218-228 and the floor of the reservoir 204 may be reduced, thereby reducing the friction between the reservoir insert 212 and the reservoir 204. This is not, however, a limiting criteria of the present disclosure.

Other embodiments of the reservoir insert 212 may be provided having different configurations. For example, protuberances on the reservoir insert 212 may have shapes other than conical. The protuberances may be provided as spheres, prisms of various geometries, polyhedrons, as well as various other regular and irregular solids. Furthermore, the present disclosure contemplates embodiments of the reservoir insert 212 that do not include protuberances. According to one embodiment, the reservoir insert 212 may be provided as a toroid. Toroidal reservoir inserts 212 may have any variety of cross-sectional geometries including, but not limited to, circular, polygonal, irregular geometries, etc.

In still another embodiment, the reservoir insert 212 may be configured as a network of linked members. For example, as a further development of the illustrated embodiment, a conical member may be disposed generally within the center of the ring of conical protuberances 218-228. The generally centrally disposed conical member may be linked to one or more of the conical protuberances 218-228 by a web that may generally resemble to the webs 230-240 connecting the ring of conical protuberances 218-228 of the reservoir insert ring member. A reservoir insert 212 according to this embodiment may be sized to translate within the reservoir 204 when contacted by a needle entering the reservoir through the septum 216. Accordingly, even the centrally disposed conical member may be displaced to permit access to the reservoir by a needle. In an alternative embodiment, however, the reservoir insert 212 may be configured only to rotate within the reservoir 204 in response to a needle contacting the reservoir insert 212. According to one such embodiment, if the needle contacts the centrally disposed conical member the needle may be deflected by the tapered profile of the centrally disposed conical member. While the foregoing description of this embodiment relates to a ring-shaped reservoir insert 212 having a centrally disposed member, the reservoir insert 212 may merely be configured as a network of members linked together, for example by a web of material extending between adjacent members, wherein at least a portion of the members may translate and/or rotate together within the reservoir 204.

According to yet another embodiment the reservoir insert 212 may include a combination of a ring/linked members and free members. For example, relating back to the illustrated embodiment of FIGS. 6 through 11, a reservoir insert 212 may be provided including a ring of linked conical protuberances 218-228. The reservoir insert 212 may additionally include a centrally disposed member that is separate from the linked protuberances 218-228. For example, a conical or spherical member may be centrally disposed within the ring of linked protuberances 218, 228. The centrally disposed member may be movable within the ring member of linked protuberances 218-228 and/or may act against and move with the ring of linked protuberances 218-228. This embodiment may differ from the previous embodiment in that the generally centrally disposed member may not be linked to the ring member.

Consistent with the foregoing description, in an embodiment in which the reservoir insert 212 includes a plurality of members, at least a portion of the members may be coupled to one another. In the case of the illustrated embodiment, the reservoir insert 212 may be configured as a ring member including a plurality of conical protuberances 218-228 that are coupled to one another by the webs 230-240. The exemplary configuration may be achieved by providing the reservoir insert 212 as a single unitary structure. For example, the conical protuberances 218-228 and the webs 230-240 may be integral components making up the ring member.

In an alternative embodiment, the conical protuberances 218-228 may be formed as separate conical members or components. The separate conical members may then be connected to one another to form the reservoir insert 212. Consistent with such an embodiment, the conical members may be mounted on a ring, or otherwise coupled together to form a generally ring shaped configuration. Accordingly, in an assembled condition, the conical members may become protuberances on a ring member. In one such embodiment, the members may be movably disposed on the ring. For example, the members may be slidably disposed on the ring such that the members may slide along the circumference of the ring. The preceding principles may also be applied to embodiments having differing configurations consistent with the present disclosure. For example, the geometry of the protuberances or members and the configuration of the ring, e.g., as a not circular member or a partial ring, may be susceptible to variation and modification.

Figure 12:
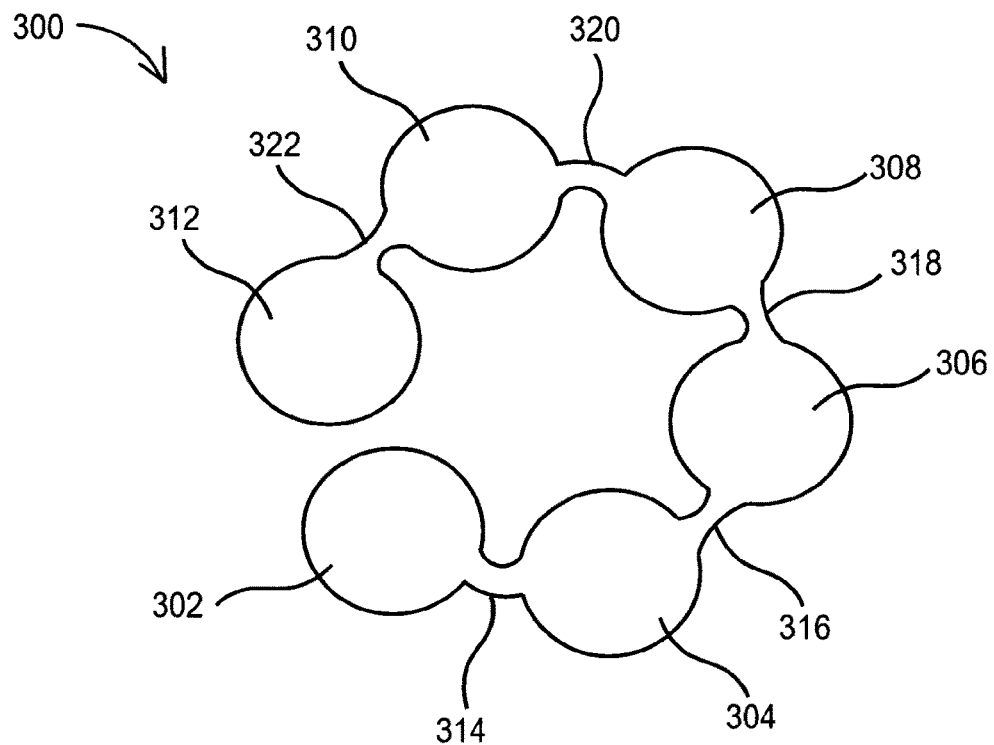
FIG. 12 is a plan view of an open-ring reservoir insert.
Figure 13:
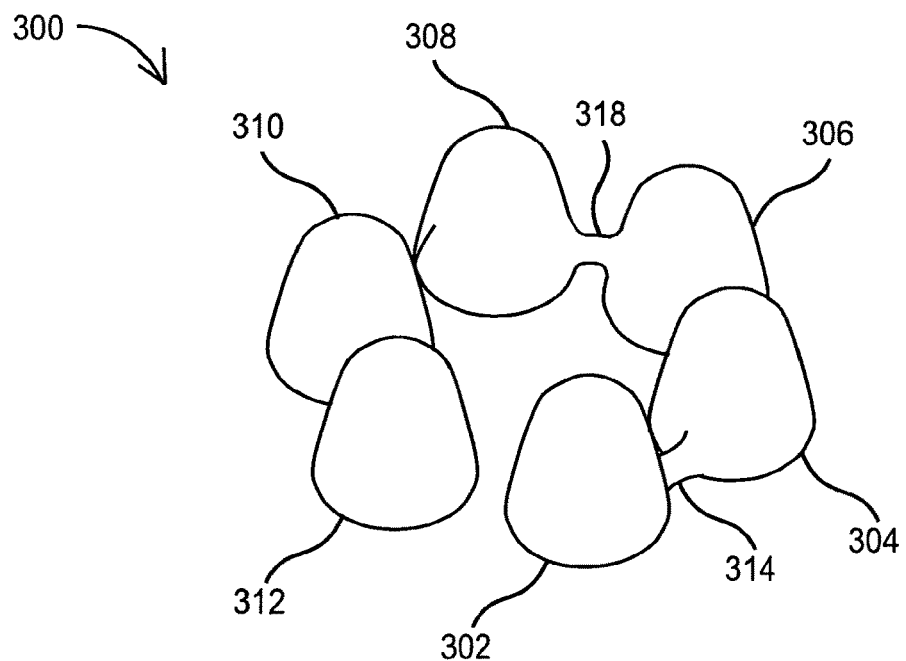
FIG. 13 is a perspective view of the open-ring reservoir insert illustrated in FIG. 12.

As used in any embodiment herein ring or ring shaped may include an open ring or a partial ring. Turning to FIGS. 12 and 13, consistent with the present disclosure, a reservoir insert 300 may be provided that is configured as an open ring or partial ring. Consistent with the illustrated embodiment, the open ring reservoir insert 300 may include a plurality of protuberances 302-312. At least a portion of the protuberances 302-312 may be connected by webs 314-322 extending between adjacent protuberances 302-312. Consistent with the aspect of an open or partial ring, at least two adjacent protuberances 312 and 302, in the case of the illustrated embodiment, may not be connected to one another by a web. The reservoir insert 300 may, therefore, be provided having an open or partial ring configuration.

As shown in the illustrated embodiment of FIGS. 12 and 13, the protuberances 302-312 may be generally conical members and may have a generally circular cross-section in the plan view of FIG. 12. As shown in FIG. 13, similar to the reservoir insert 212 of FIGS. 7, 9, and 10, the protuberances 302-312 of the open ring reservoir insert 300 may have a generally rounded apex, rather than a point. Similarly, the protuberances 302-312 may be formed having an arcuate base. According to various alternative embodiments, conical protuberances 302-312 herein may be provided having a flat base and/or a pointed apex. Furthermore, the protuberances 302-312 may be provided having geometries other than conical. For example, the protuberances may be spherical, oval, polygonal, have an irregular shape, etc. Accordingly, the shape of the protuberance should not be considered limiting on any embodiment herein.

Consistent with still further embodiments, an open or partial ring reservoir insert may be provided that does not include any protuberances. According to one such embodiment, the open or partial ring reservoir insert may be provided having a uniform cross-sectional geometry. However, in other embodiments an open or partial ring reservoir may be provided having a varying cross-sectional geometry and/or area.

According to various alternative embodiments, the open or partial ring reservoir insert may be provided having an even greater open configuration, for example, the partial ring reservoir insert may be provided as a half circle, C-shaped member, etc. According to further embodiments consistent with the present disclosure, more than one partial ring reservoir insert may be provided disposed in the reservoir. Accordingly, as used in any embodiment herein, ring, ring shaped member, partial ring, or open ring may include members having a curved geometries, including circular and/or oval geometries, polygonal geometries, as well as combinations thereof.

There is thus provided a vascular access portal that may provide more efficient flushing and may reduce the accumulation of precipitates and/or residue in the access portal. An access portal consistent with the present disclosure may generally include a housing, and a body defining a fluid reservoir. According to one aspect, the fluid reservoir may optionally have a teardrop shape that promotes fluid passage between the stem and the reservoir while minimizing hang-up within the reservoir. A septum may be disposed on the housing, thereby enclosing the fluid reservoir. A stem may be provided in fluid communication with the fluid reservoir through an outlet passage extending form the fluid reservoir. Consistent with another aspect, the outlet passage extending providing fluid communication between the fluid reservoir and the stem may extend from the fluid reservoir at an angle. Furthermore, the outlet passage may extend tangentially from the fluid reservoir. The access portal may also include a reservoir insert disposed within the fluid reservoir. The reservoir insert may reduce the fluid fill volume of the fluid reservoir. According to one aspect, the reservoir insert may include a ring and/or a ring having a plurality of protuberances. Consistent with the foregoing description, the access portal may include a plurality of non-movable volume reduction members projecting from only a portion of at least one of a bottom or a sidewall of a fluid reservoir.

The description hereinabove is directed at exemplary embodiments consistent with the claimed subject matter. It should be understood, however, that the features and aspects of the various embodiments may be combined with one another to achieve still further embodiments consistent with the present disclosure. Additionally, the described embodiments are susceptible to further modification and variation without materially departing from the invention set forth in the claims appended hereto.

What is claimed is:

1. An access portal comprising:
   a fluid reservoir configured to receive a portion of an injection device, said fluid reservoir including a base region and at least one sidewall extending upward from said base region to define an open region;
   a septum separate from and coupled to said fluid reservoir to seal said open region of said fluid reservoir, said septum having an underside at least partially exposed to said fluid reservoir; and
   a plurality of non-movable volume reduction members disposed within said fluid reservoir, said plurality of said volume reduction members each having an upper surface which tapers towards said septum and is configured to contact and deflect a tip of said injection device inserted through said open region and said septum, said plurality of volume reduction members having at least one dimension approximately equal to a distance between said base region of said fluid reservoir and said underside of said septum.

2. The access portal according to claim 1, further comprising a stem in fluid communication with said fluid reservoir via an outlet passage.

3. The access portal according to claim 1, further comprising a web configured to couple said plurality of volume reduction members together.

4. The access portal according to claim 1, further comprising a housing at least partially surrounding said fluid reservoir.

5. The access portal according to claim 4, wherein said housing defines an opening on a top surface thereof, said opening defining a curved margin shaped and sized to guide the injection device in a direction of said septum.

6. An access portal comprising:
   a fluid reservoir;
   a septum sealing an open region of said fluid reservoir;
   a housing defining an opening circumscribing an outer perimeter of said septum, said opening including an angled margin to urge a portion of an injection device towards said septum and into said fluid reservoir; and
   a plurality of non-movable volume reduction members projecting from only a portion of at least one of a bottom or a sidewall of said fluid reservoir, said plurality of volume reduction members each having an upper surface which tapers towards said septum and is configured to contact and deflect a tip of said injection device inserted through said open region and said septum and configured to reduce a fluid fill volume of said fluid reservoir.

7. The access portal according to claim 6, wherein said plurality of volume reduction members project from said bottom of said fluid reservoir.

8. The access portal according to claim 6, wherein said plurality of volume reduction members project from said sidewall of said fluid reservoir.

9. The access portal according to claim 6, wherein said plurality volume reduction members generally define a central region, said central region extending unobstructed from said base of said fluid reservoir to said septum.

10. The access portal according to claim 6, further comprising a stem in fluid communication with said fluid reservoir via an outlet passage.

11. The access portal according to claim 6, further comprising a body at least partially defining said fluid reservoir.

12. An access portal comprising:
   a fluid reservoir;
   a septum sealing an open region of said fluid reservoir, said septum having an underside at least partially exposed to said fluid reservoir;
   a plurality of non-movable spherical volume reduction members disposed within said fluid reservoir, each of said plurality of volume reduction members having a diameter approximately equal to a height between a bottom of said fluid reservoir and said underside of said septum.

13. The access portal according to claim 12, wherein said plurality of volume reduction members are coupled to one another via a web to form a ring member.

14. The access portal according to claim 13, wherein said ring member generally defines a central region, said central region extending unobstructed from a base of said fluid reservoir to said septum.

15. The access portal according to claim 12, wherein said plurality of volume reduction members extend from at least one of said bottom or a sidewall of said fluid reservoir.

16. The access portal according to claim 12, further comprising a stem in fluid communication with said fluid reservoir via an outlet passage.

17. The access portal according to claim 12, further comprising a housing defining an opening on a top surface thereof, said opening defining a margin portion shaped and sized to guide an injection device in a direction of said septum.

* * * * *